(12) United States Patent
Jones et al.

(10) Patent No.: US 6,218,164 B1
(45) Date of Patent: *Apr. 17, 2001

(54) THERMOPALLIUM BACTERIA AND ENZYMES OBTAINABLE THEREFROM

(75) Inventors: Brian E. Jones, Leidschendam; Margareta A. Herweijer, The Hague, both of (NL); Michael J. Danson, Saltford (GB); David W. Hough; Carl R. Thompson, both of Bath (GB)

(73) Assignee: Genencor International, Inc., Rochester, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,937

(22) PCT Filed: Sep. 3, 1996

(86) PCT No.: PCT/EP96/03896

§ 371 Date: Jun. 2, 1998

§ 102(e) Date: Jun. 2, 1998

(87) PCT Pub. No.: WO97/10342

PCT Pub. Date: Mar. 20, 1997

(30) Foreign Application Priority Data

Sep. 13, 1995 (EP) .................................................. 95202477

(51) Int. Cl.[7] .............................. C12N 9/26; C12N 9/44; C12P 19/16; D21C 1/00; C11D 3/00

(52) U.S. Cl. ........................... 435/210; 435/201; 435/98; 435/277; 435/278; 510/300; 510/305

(58) Field of Search ............................. 435/210, 98, 277, 435/278, 201; 510/300, 305

(56) References Cited

U.S. PATENT DOCUMENTS

| | | | |
|---|---|---|---|
| 4,628,031 | * | 12/1986 | Zeikus et al. ........................ 435/205 |
| 4,929,557 | * | 5/1990 | Antranikian et al. ................. 435/202 |
| 5,055,403 | * | 10/1991 | Tomimura ............................. 435/210 |
| 5,486,469 | * | 1/1996 | Antranikian et al. ................. 435/210 |
| 5,736,375 | * | 4/1998 | Deweer et al. ....................... 435/210 |
| 5,817,498 | * | 10/1998 | Deweer et al. ...................... 435/252.3 |

FOREIGN PATENT DOCUMENTS

0410498 * 1/1989 (EP) .

OTHER PUBLICATIONS

Li, Y., et al., International Journal of Systematic Bacteriology, vol. 44, "Clostridium thermoalcaliphilum sp. nov., an anaerobic and thermotolerant facultative alkaliphile", pp. 111–118, 1994.*

Lee, S.–P., et al., Applied and Environmental Microbiology, vol. 60, Cloning of the aapT gene and characterization of its product, alpha–amylase–pullulanase (Aapt) from thermophilic and alkaliphilic Bacillus sp. strain XAL601, pp. 3764–3773, 1994.*

Engle, M., et al., "International Journal of Systematic Bacteriology, vol. 45, Isolation and characterization of a novel alkalitolerant thermophile, Anaerobranca horikoshii gen. nov., sp. nov.", pp. 454–461, 1995.*

Ravot., G., et al., EMBL datase entry ID TE16SRNA, Accession No. X80790, "Thermotoga elfii 16S ribosomal RNA gene", 1519bp, 1995.*

Jones, B.E., et al., EMBL database entry ID TN16SRRNA, Accession No. X91822, "Thermopallium natronophilum 16S ribosomal RNA", 1437bp, 1995.*

Duckworth, A. W., et al., FEMS Microbiology Ecology, vol. 19, "Phylogenetic diversity of soda lake alkaliphiles", pp. 181–191, 1996.*

* cited by examiner

Primary Examiner—Ponnathapu Achutamurthy
Assistant Examiner—William W. Moore
(74) Attorney, Agent, or Firm—Lynn Marcus-Wyner; Genencor International, Inc.

(57) ABSTRACT

The present invention provides thermophilic alkaliphilic bacteria designated *Thermopallium natronophilum* and thermophilic alkaliphilic polypeptides obtainable therefrom. It also provides compositions, particularly detergent compositions comprising the polypeptides.

10 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1437 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (vi) ORIGINAL SOURCE:
      (A) ORGANISM: Thermopallium natronophilum
      (B) STRAIN: Tg9A
      (C) INDIVIDUAL ISOLATE: DSM 9460

(ix) FEATURE:
      (A) NAME/KEY: misc_RNA
      (B) LOCATION: 1..1437
      (D) OTHER INFORMATION: /partial
         /product= "16S ribosomal RNA"

(xi) SEQUENCE DESCRIPTION: SEQ ID NO: 1:

```
CTGNCGGCGT GCCTAACACA TNCAAGTCGA GCGGTGCTAC GGAGGTCTTC GGACTGAAGT     60

AGCATAGCGG CGGACGGGTG AGTAATACAC AGGAACGTGC CCCTTGGAGG CGGATAGCTG    120

TGGGAAACTG CAGGTAATCC GCCGTAAGCT CGGGAGAGGA AAGCCGGAAG GCGCCGAGGG    180

AGCGGCCTGT GGCCCATCAG GTAGTTGGTA GGGTAAGAGC CTACCAAGCC GACGACGGGT    240

AGCCGGTCTG AGAGGATGGA CGGCCACAAG GGCACTGAGA CACGGGCCCT ACTCCTACGG    300

GAGGCAGCAG TGGGGATAT TGGACAATGG GCGAAAGCCT GATCCAGCGA CGCCGCGTGA    360

GGGACGAAGT CCTTCGGGAC GTAAACCTCT GTTGTAGGGG AAGAAGACAG TGACGGTACC    420

CTACGAGGAA GCCCCGGCTA ACTACGTGCC AGCAGCCGCG GTAATACGTA GGGGNCGAGC    480

GTTACCCGGA ATCACTGGGC GTAAAGGGTG CGTAGGCGGT CTAGCAAGTC TGGCCTTAAA    540

GACCACGGCT CAACCGTGGG GATGGGCTGG AAACTGTTAG ACTTGAGGGC ACTAGAGGCA    600

GACGGAACTG CTGGTGTAGG GGTGAAATCC GTAGATATCA GCAGGAACGC CGGTGGAGAA    660

GTCGGTCTGC TGGGGTGACC CTGACGCTGA GGCACGAAAG CTAGGGGAGC GAACCGGATT    720

AGATACCCGG GTAGTCCTAG CCGTAAACGA TGCTCACTAG GTGTGGGGGA GTAAATCCTC    780

CGTGCTGAAG CTAACGCGAT AAGTGAGCCN CCTGGGGAGT ACGCCCNCAA GGGTGAAACT    840

CAAAGGAATT GACGGGGGNC CGCACAANCG GTGGAGCGTG TGGTTTAATT GGAAGCTAAG    900

CCAAGAACCT TACCAGGGTT TGACATTCTG GTGGTACCGA NCCGAAAGGT GAGGGACTCT    960

TCACTTAGGT GGAGGGAGCC AGCACAGGTG GTGCACGGTC GTCGTCAGCT CGTGCCGTGA   1020

GGTGTTGGGT TAAGTCCCGC AACGAGCGCA ACCCCTGCCC TTAGTTGCCA GCACGTAAAG   1080

GTGGGCACTC TAAGGGGACT GCCTGCGACG AGCAGGAGGA AGGAGGGGAT GACGTCAGAT   1140

ACTCGTGCCC CTTATGCCCT GGGCGACACA CGCGCTACAA TGGGCAGGAC AAAGGGAAGC   1200

GAGCCGGCGA CGGTGAGCAA ATCCCAAAAA CCTGCCCCCA GTTCAGATTG TGGGCTGAAA   1260

CCCGCCCACA TGAAGCCGGA ATCGCTAGTA ATCGTGGATC AGCCACGCCA CGGTGAATAC   1320

GTNCCCGGGN CTTGTACACA CCGCCCGTCA AGCCACCCGA GTTGGGGGNA CCCGAAGATA   1380

CGTACCCTTA GGGGGCGTAT TTAGGGTGAA CCTGGTGAGG GGGGGTNGTC GGAAGTC      1437
```

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Thermopallium natronophilum
        (B) STRAIN: Tg9A
        (C) INDIVIDUAL ISOLATE: DSM 9460

(xi) SEQUENCE DESCRIPTION: SEQ ID NO: 2:

```
Xaa Xaa Glu Ile Ile Tyr Xaa Gly Phe
1               5
```

(2) INFORMATION FOR SEQ ID NO: 3:

(i) SEQUENCE CHARACTERISTICS:
        (A) LENGTH: 20 amino acids

```
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: Thermopallium natronophilum
            (B) STRAIN: Tg9A
            (C) INDIVIDUAL ISOLATE: DSM 9460

(xi) SEQUENCE DESCRIPTION: SEQ ID NO: 3:

Tyr Ile Gly Asp Gly Ala Trp Glu Ala Val Leu Glu Gly Asp Asp Glu
1               5                  10                  15

Xaa Phe Tyr Arg
            20

(2) INFORMATION FOR SEQ ID NO: 4:

(i) SEQUENCE CHARACTERISTICS:
            (A) LENGTH: 27 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: Thermopallium natronophilum
            (B) STRAIN: Tg9A
            (C) INDIVIDUAL ISOLATE: DSM 9460

(xi) SEQUENCE DESCRIPTION: SEQ ID NO: 4:

Ile Gly Leu Pro Ser Val Met Thr Glu Pro Trp Asn Pro Ile Gly Gly
1               5                  10                  15

Ser Asn Trp Ile Phe Asp Met Met Leu Ile Arg
            20                  25
```

THERMOPALLIUM BACTERIA AND ENZYMES OBTAINABLE THEREFROM

TECHNICAL FIELD OF THE INVENTION

The present invention relates to novel alkaliphilic and thermophilic microorganisms and to novel enzymes obtained therefrom.

BACKGROUND OF THE INVENTION

Alkaliphiles are a heterogeneous group of microorganisms spread over many taxonomic groups which exhibit optimum growth in an alkaline pH environment (Jones, B. E. et al, (1994) Alkaliphiles: diversity and identification, in "*Microbial Diversity and Identification*" (F. G. Priest et al, Eds.) Plenum Press, New York and London, pages 195–230), generally in excess of pH 8. Obligate alkaliphiles generally have a pH optimum for growth between pH 9 and pH 10, and are incapable of growth at neutral pH. Alkalitolerant (or facultatively alkaliphilic) microorganisms are less exacting and although they are capable of growth at alkaline pH values, their optima lie in the neutral to acid pH range.

Thermophiles are also a very heterogeneous collection of microorganisms defined as having an optimum growth temperature in excess of 50° C. For moderate thermophiles the maximum growth temperature usually lies below 70° C. An organism with a growth minimum above 40° C., an optimum above 65° C., and a growth maximum above 70° C. is defined as an extreme thermophile (Cowan, D. A. (1992) Biochemistry and molecular biology of extremely thermophilic archeaobacteria, in "*Molecular Biology and Biotechnology of Extremophiles*" (R. A. Herbert and R. J. Sharp, Eds.), Blackie & sons Ltd., Glasgow and London, pages 1–43).

The combined phenotype, alkaliphily and thermophily appears to have only rare occurrence. Only two such microorganisms, both isolated from sewage digestion plants, have been well described and both were assigned to the genus Clostridium of the Gram-positive bacteria. One of the organisms, *Clostridium paradoxum*, is obligately alkaliphilic growing between pH 7.3 and pH 11.0, with an optimum around pH 10. It can however, only be classified as a moderate thermophile since it has an optimum growth temperature of 55° C. and a maximum at 63° C. (Youhong Li et al (1992) Int. J. Syst. Bacteriol. 43, 450–460). A second organism, *Clostridium thermoalcaliphilum* is a facultative alkaliphile or alkalitolerant organism growing between pH 7 and pH 11, with an optimum between pH 9.5 and pH 10. With an optimum growth temperature of 50° C. and maximum at 57° C. this bacterium can only be classified as a very moderate thermophile or as thermotolerant (Youhong Li et al (1994) Int. J. Syst. Bacteriol. 44, 111–118).

Among the known types of thermophilic bacteria several species belong to the order Thermotogales. This distinct group of mainly extreme thermophilic bacteria has been shown by sequencing of the ribosomal RNA genes to be phylogenetically distant from all other bacteria, and to represent one of the deepest branches and most slowly evolving lineages within the Domain Bacteria. Bacteria of the Thermotogales are characteristically, Gram-negative, rod-shaped, anaerobic, fermentative bacteria with an outer sheath-like envelope ("toga"); their growth is inhibited by molecular hydrogen (Huber, R. and Stetter, K. O. (1992) The order Thermotogales, in "*The Prokaryotes*" (A. Balows et al, Eds.), Springer-Verlag, New York, pages 3809–3815).

At present, the Thermotogales are represented by five genera. The genera Thermotoga, Thermosipho and Fervidobacterium comprise the known extreme thermophilic species, while the more distantly related (on the basis of 16S rRNA analysis) genera Geotoga and Petrotoga represent the more mesophilic species. None of the known species is noticeably alkaliphilic in nature. Most of the extant species of extreme thermophilic Thermotogales have been isolated from active geothermal aquatic environments such as shallow and deep-sea marine hydrothermal systems or from low-salinity continental solfatara springs. More recently less thermophilic strains, particularly those of the genera Geotoga and Petrotoga have been isolated from deep subsurface oil fields (Huber, R. and Stetter, K. O. (1992) ibid; Davey, M. E. et al, (1993) Syst. Appl. Microbiol. 16, 191–200; Ravot, G. et al, (1995) Int. J. Syst. Bacteriol. 45, 308–314).

Although the different members of the Thermotogales may be partially differentiated on the basis of phenotypic characteristics such as temperature, pH and NaCl ranges permitting growth (Table 1, Ravot, G. et al (1995) Int. J. Syst. Bacteriol. 45, 308–314), their classification is largely based on a comparison of similarity between nucleotide sequences on the 16S rRNA genes and DNA-DNA hybridisation studies. Stackebrandt and Goebel (Int. J. Syst. Bacteriol. 44, 846–849, 1994) suggest that strains of microorganisms having more than 97% 16S rRNA sequence identity may be considered members of the same species, provided that other criteria are also met. It has been shown that the 16S rRNA sequences of *Fervidobacterium islandicum* and *Fervidobacterium nodosum* are 95.3% similar which is typical of different species within the same genus (Huber, R. et al, (1990) Arch. Microbiol. 154, 105–111), but that these differ by 10–15% with strains of Thermotoga and Thermosipho. Within the Thermotogales sequence differences of up to about 8% have generally qualified for placing the strains in the same genus. 16S rRNA sequence differences of greater than about 10%, together with differences in phenotype have frequently been used as compelling arguments for placing different isolates of Thermotogales in separate genera (Huber, R. et al, (1989) Syst. Appl. Microbiol. 12, 32–37; Davey, M. E. et al, (1993) Syst. Appl. Microbiol. 16, 191–200; Ravot, G. et al, (1995) Int. J. Syst. Bacteriol. 45, 308–314).

TABLE 1

Some characteristics that differentiate member of the Thermotagales

| GENUS | SPECIES | TEMPERATURE ° C. | | pH | | NaCl CONCENTRATION (%) | | G + C CONTENT (mol %) | REFERENCE |
|---|---|---|---|---|---|---|---|---|---|
| | | RANGE | OPTIMUM | RANGE | OPTIMUM | RANGE | OPTIMUM | | |
| Thermotoga | maritima | 55–90 | 80 | 5.5–9 | 6.5 | 0.25–3.75 | 2.7 | 46 | 1 |
| | neapolitana | 55–90 | 80 | 5.5–9 | 7 | | | 41 | 2 |
| | thermarum | 55–84 | 70 | 5.5–9 | 7 | 0.2–0.55 | 0.35 | 40 | 3 |
| | elfii | 50–72 | 66 | 5.5–8.7 | 7.5 | 0–2.8 | 1.2 | 39.6 | 4 |

TABLE 1-continued

Some characteristics that differentiate member of the Thermotagales

| GENUS | SPECIES | TEMPERATURE ° C. | | pH | | NaCl CONCENTRATION (%) | | G + C CONTENT (mol %) | REFERENCE |
|---|---|---|---|---|---|---|---|---|---|
| | | RANGE | OPTIMUM | RANGE | OPTIMUM | RANGE | OPTIMUM | | |
| | sp.FjSS3 | 55–90 | 80 | 4.8–8.2 | 7 | | | 45.8 | 5 |
| Thermosipho | africanus | 35–77 | 75 | 6–8 | 7.2 | 0.11–3.6 | | 29 | 6 |
| Fervidobacterium | nodosum | 41–79 | 70 | 6–8 | 7 | | 0.1 | 33.7 | 7 |
| | islandicum | 50–80 | 65 | 6–8 | 7.2 | | 0.2 | 41 | 8 |
| | pennavorens | | 70 | | 6.5 | | | 40 | 9 |
| Petrotoga | miotherma | 35–65 | 55 | 5.5–9 | 6.5 | 0.5–10 | 2 | 39.8 | 10 |
| Geotoga | petraea | 30–55 | 50 | 5.5–9 | 6.5 | 0.5–10 | 3 | 29.5 | 10 |
| | subterranea | 30–60 | 45 | 5.5–9 | 6.5 | 0.5–10 | 4 | 29.9 | 10 |
| Thermopallium | natronophilum | 52–78 | 70 | 7.2 > 10.5 | 9.2 | 0–5 | 1 | 36.3 | 11 |

1. Huber, R. et al (1986) Arch. Microbiol. 144, 324–333.
2. Jannasch, H. et al (1988) Arch. Microbiol. 150, 103–104.
3. Windburger, E. et al (1989) Arch. Microbiol. 151, 506–512.
4. Ravot, G. et al (1995) Int. J. Syst. Bacteriol. 45, 308–314.
5. Huser, B.A. et al (1986) FEMS Microbiol. Letts. 37, 121–127; Janssen, P.H. and Morgan, H.W. (1992) FEMS Microbiol. Letts. 96, 213–218.
6. Huber, R. et al (1989) Syst. Appl. Microbiol. 12, 32–37.
7. Patel, B.K. et al (1985) Arch. Microbiol. 141, 63–69.
8. Huber, R. et al (1990) Arch. Microbiol. 154, 105–111.
9. WO 93/18134.
10. Davey, M.E. et al (1993) Syst. Appl. Microbiol. 16, 191–200.
11. The microorganisms of the present invention.

SUMMARY OF THE INVENTION

The present invention provides novel thermophilic alkaliphilic bacteria of the novel genus Thermopallium, more specifically of the novel species *Thermopallium natronophilum*, and novel polypeptides obtainable from these bacteria. In a more specific aspect, the invention provides novel alkaline pullulanase and amylase preparations from these novel bacteria.

In a third aspect, the invention provides a composition comprising a novel polypeptide according to the invention.

In a fourth aspect, the invention provides an isolated DNA fragment encoding a polypeptide according to the invention, recombinant DNA comprising such DNA fragment, host cells transformed with such recombinant DNA and a culture of such host cells.

In another aspect, the invention provides a method for producing a polypeptide, preferably an enzyme, according to the invention.

DETAILED DISCLOSURE OF THE INVENTION

The microorganisms

The novel microorganisms of the present invention were isolated from hot springs and their run-off streams having an alkaline pH due to dissolved carbonate (and related anions) but having a low concentration of dissolved salts as measured by electrical conductivity (Table 2). The hot springs were located in the volcanically active regions of the Rift Valley in continental East Africa. They have typical carbonate anion concentrations in excess of 1 g/l and are therefore not typical of the usual solfatara type. A pure culture of the isolated microorganism designated *Thermopallium natronophilum* Tg9A has been deposited on Sep. 21, 1994 according to the Budapest Treaty on the International Recognition of the Deposits of Microorganisms for the Purpose of Patent Procedures at the DSM-Deutsche Sammlung von Mikroorganismen und Zelikulturen GmbH, Mascheroder Weg 1b, D-38124 Braunschweig, Germany under Accession Number DSM 9460.

TABLE 2

Characteristics of hot, alkaline springs containing Thermopallium.

| SITE | TEMPERATURE ° C. | pH | CONDUCTIVITY mS/cm | Thermopallium |
|---|---|---|---|---|
| 1 | 66 | 9.5 | 8 | strain Tg7A1 |
| 2 | 85 | 10 | 18 | — |
| 3 | 96 | 8.5 | 4.8 | strain Tg9A |
| 4 | 60–80 | 9.8 | 35 | — |
| 5 | 60–80 | 9.8 | 37 | — |

The microorganism of this invention is a strictly anaerobic, rod-shaped bacterium which does not form endospores. The bacterial cell is surrounded by a characteristic sheath-like outer structure or "toga" ballooning over both poles of the cell. The cells usually occur singly or in short chains of up to 3 cells long. During the growth phase the cells can become curved or irregular in shape, and sometimes form aggregates. During the stationary growth phase the cells become coccoid, with one or more cells inside a large spherical body. The microorganism forms round, shiny, whitish, translucent colonies on alkaline nutrient agar or Gelrite, containing carbonate. On the basis of these characteristics the strains of the microorganism *Thermopallium natronophilum* can therefore be assigned to the bacterial order "Thermotogales" (Huber, R. and Stetter, K. O. (1992) The order "Thermotogales" in: *The Prokaryotes*, (A. Barlows et al., eds.), Springer-Verlag, New York, pp. 3809–3815).

The natural isolates of the microorganism of the present invention can be further described by the following characteristics.

Growth temperature: they grow between 52° C. and 78° C., no growth at 50° C. or at 79° C. The maximum growth rate was observed at about 70° C. whereas the maximum cell yield was obtained at from about 63° to about 64° C.

Growth pH: pH in range: 7.2 to >10.5 supports growth. pH optimum: about 8.8 to about 9.5

Influence of NaCl: the optimum NaCl concentration for growth is 1% (w/v), with no growth above 4–5% (w/v).

Gram reaction: negative.

KOH reaction: negative.

Aminopeptidase reaction: negative.

Effect of SDS: in the presence of sodium dodecylsulphate 1%, (w/v) both the cells and the the sheath-like structures disappear under the microscope within a few seconds.

Effect of lysozyme: when lysozyme (10 mg/ml) was added to a suspension of cells under the microscope, little effect was observed. At 20 mg/ml lysozyme some of the rod-shaped cells became spherical.

Growth on glucose: positive.
- galactose: positive.
- maltose: positive.
- xylose: weak.
- ribose: negative.
- formate: negative.
- acetate: positive.
- lactate: negative.
- propionate: negative.
- pyruvate: weak.
- glutamate: negative.
- glycine: positive.
- glycerol: positive.
- ethanol: negative.
- cellulose: positive.
- casein: positive.
- gelatine: positive.
- xylan: positive.
- starch: positive.
- olive oil: positive.
- tryptone: positive.

Influence of sulphur and hydrogen on growth: growth is inhibited by molecular hydrogen, $H_2$. This inhibition may be relieved by the addition of sulphur to the medium.

G+C content: 36.3±0.9 Mol % (n=2) (HPLC method).

Classification and Identification of the Microorganism

The strains of the invention were classified on the basis of phylogenetic relationships by direct sequencing of the 16S rRNA genes amplified by PCR. Sequences were compared with sequences for known bacteria accessed from GenBank and EMBL databases. Sequences were aligned and subjected to phylogenetic analysis using computer programs (versions 3.4 and 3.5c of the PHYLIP package (Felsenstein, J. (1989) Cladistics 5, 164–166)). Similarity values were computed (Table 3) and a phylogenetic tree constructed.

The results indicate that the strains have a 16S rRNA sequence similarity of 98.7% and thus may be considered as isolates of the same species. The results further indicate that the strains of the new microorganism are more closely related to the genus Fervidobacterium than to bacteria of any other genus. However, the strains of the new microorganism have an outer sheath-like structure, often referred to as the 'toga' which is expanded over both poles of the rod-shaped cells. This 'toga' is a common feature of members of the genera Thermotoga, Thermosipho, Geotoga and Petrotoga Balows et al., Eds.) Springer-Verlag, New, York, p. 3809–3815; Ravot, G. et al., (1995) International journal of Systematic Bacteriology 45, 308–314). In contrast, Fervidobacterium species have a terminai 'spheroid' (Huber, R. and Stetter, K. O. ibid; Huber, R. et al., (1990) Archives of Microbiology 154, 105–111; Patel, B. K. C. et al., (1985) Archives of Microbiology 141, 63–69). This evidence alone indicates that the strains of the new microorganism represent a novel species. However, the difference in sequence homology of almost 10% with Fervidobacterium is highly significant since these lineages which represent one of the deepest branches of the Domain Bacteria (Winkler, S. and Woese, C. R. (1991) Systematic & Applied Microbiology 13, 161–165) are evolving slowly relative to other bacterial lineages (Huber, R. et al., Systematic & Applied Microbiology 12, 32–37). This indicates that the new bacterium is of a separate and hitherto unknown genus. On this basis the microorganism is assigned to the new genus, Thermopallium; and the strains of the microorganism to the species, *Thermopallium natronophilum*. The genus Thermopallium and the species *Thermopallium natronophilum* are defined by the nucleotide sequence of the 16S rRNA gene (SEQ ID No. 1 of the attached sequence listing), and by the phenotypic characteristics described herein.

The difference in G+C value compared with those of known species (Table 4) further supports the assignment of these new strains of the microorganism to a new species. The phenotypic characteristics of the microorganisms of the present invention clearly set them apart from the known species of the Thermotogales (Table 1). The novel microorganisms are clearly extreme thermophiles and have a temperature profile typical of Thermotogales species isolated from continental hot springs (i.e. non-marine sources). However, the known species of the Thermotogales all have pH optima for growth around neutrality. In contrast, the novel microorganisms of this invention are clearly obligately alkaliphilic and are unable to grow at neutral pH (Table 1) or without a medium containing carbonate anions.

TABLE 3

16S rDNA similarity values

|   | 1 | 2 | 3 | 4 | 5 | 6 | 7 | 8 | 9 | 10 |
|---|---|---|---|---|---|---|---|---|---|---|
| 1. *Thermopallium natronophilum* Tg9A | | | | | | | | | | |
| 2. *Thermopallium natronophilum* Tg7A1 | 98.7 | | | | | | | | | |
| 3. *Fervidobacterium islandicum* | | 90.9 | | | | | | | | |
| 4. *Fervidobacterium pennavorens* | | 90.7 | 98.8 | | | | | | | |
| 5. *Fervidobacterium nodosum* | | 90.7 | 96.4 | 96.1 | | | | | | |
| 6. *Thermosipho africanus* | | 88.4 | 90.3 | 90.4 | 89.5 | | | | | |
| 7. *Thermotoga maritima* | | 85.9 | 87.4 | 87.8 | 88.0 | 91.0 | | | | |
| 8. *Thermotoga thermarum* | | 84.6 | 87.1 | 87.2 | 86.5 | 90.6 | 92.5 | | | |
| 9. *Geotoga petraea* | | 83.0 | 82.4 | 83.1 | 83.0 | 82.5 | 82.5 | 81.4 | | |
| 10. *Petrotoga miotherma* | | 80.6 | 81.3 | 81.3 | 81.8 | 80.8 | 80.0 | 78.9 | 86.6 | |

TABLE 4

| G + C values (Mol %) | |
|---|---|
| 1. Thermopallium natronophilum | 36.3 |
| 2. Fervidobacterium islandicum | 40 |
| 3. Fervidobacterium pennavorens | 40.0 |
| 4. Fervidobacterium nodosum | 33.7 |
| 5. Thermosipho africanus | 30 |
| 6. Thermotoga maritima | 46 |
| 7. Thermotoga thermarum | 40 |
| 8. Geotoga petraea | 29.5 |
| 9. Petrotoga miotherma | 39.8 |

Cultivation of the Microorganism

The microorganism of the present invention can be cultivated only under strictly anoxic conditions, for example in a Freter type anaerobic cabinet or in closed bottles using the strictly anaerobic techniques described by Balch et al. (Microbiol. Rev. (1979), 43, 260–296). A suitable nutrient medium is required, Typically, such a medium comprises an assimilable carbon and nitrogen source together with other essential nutrients. Preferably, the total dissolved salt concentration of the medium does not exceed a conductivity value of about 15 mS/cm, and is prepared under the strictly anaerobic conditions indicated above. Preferably, a reductant is added to give a sufficiently low initial redox value. Suitable media can be prepared by techniques known in the art.

Since the natural isolates of the novel microorganisms of the novel species *Thermopallium natronophilum* of the present invention are alkaliphilic and are unable to grow below pH 7.2, the cultivation is preferably conducted at alkaline pH values which can be achieved by the addition of suitable buffers such as sodium carbonate, or more preferably mixtures of sodium carbonate and sodium bicarbonate, after sterilization of the growth medium, and preferably under a head space gas phase of $O_2$-free $N_2$. Such a medium is TMZ-medium which is a modification of Thermus medium using Castenholtz salts (Williams, R. A .D. and Da Costa, M. S. (1992) The genus Thermus and related microorganisms, in: *The Prokaryotes* (A. Barlows et al., eds.), Springer-Verlag, New York, p. 3745) adapted to the original conditions in the hot spring water from which the microorganism was isolated in pure culture. Growth is possible in other buffer mixtures such as Tris/HCl or Borax/NaOH provided that the pH is adjusted with carbonate. Little or no growth is obtained on media adjusted to alkaline pH values with NaOH.

For cultivation on a large scale it is typically necessary to sparge the medium continuously using $O_2$-free nitrogen gas. minimum temperature for growth was about 40° C. In a preferred embodiment, isolates of the novel species *Thermopallium natronophilum* were grown at 65° C.

After fermentation, liquid enzyme concentrates may be obtained by separation of the cells from the culture broth and concentration of the broth using methods known in the art. Alternatively, the cells may be suspended in a suitable liquid and broken open, disintegrated, or dissolved, or otherwise treated to release enzymes in a soluble fraction, using appropriate methods. The solubilised enzymes may be purified, optionally after concentrating and/or precipitated in a solid form by the use of salts or water miscible solvents or removal of water. The purified enzymes may finally be obtained in a crystalline form.

Enzymes from the Microorganism

The enzymes of this invention are obtainable by the cultivation of a microorganism of the invention, preferably *Thermopallium natronophilum* Tg9A, DSM 9460, or a variant or mutant thereof, in an appropriate nutrient medium maintained at an alkaline pH, for example pH 7.5 to 12.0, or more preferably pH 8.5 to 9, by the addition of carbonate, or mixtures of carbonate and bicarbonate, containing carbon and nitrogen sources and inorganic salts.

A mutant or variant strain of *Thermopallium natronophilum* may be obtained spontaneously, chemically, by genetic manipulation techniques or otherwise and include mutants obtained by nucleic acid transfer, environmental selection pressure, UV radiation and by the use of mutagenic chemicals known to those skilled in the art.

The enzymes may also be obtained by recombinant DNA technology by cloning the appropriate genes in a suitable host organism. This may be achieved by any suitable means, and for example by digesting chromosomal DNA with one or more restriction enzymes to create a genomic library or random DNA fragments of one size. The DNA fragments from the library of the random fragments may be inserted into a recombinant nucleic acid. Such a recombinant nucleic acid is typically a vector, which may, for example, be a plasmid, a bacteriophage or any other construct which is suitable for the transfer, or for the transfer and expression, of nucleic acid sequences.

Those of skill in the art will be able to prepare suitable vectors starting with widely available vectors which will be modified by genetic engineering techniques known in the art, such as those described by Sambrook et al (Molecular cloning: a Laboratory Manual; 1989).

A vector of the invention typically comprises one or more origins of replication so that it can be replicated in a host cell, such as bacterial cell or yeast cell (this enables constructs to be replicated and manipulated, for example in *E. coli*, by standard techniques of molecular biology). A vector also typically comprises at least the following elements, usually in a 5' to 3' arrangement: a promoter for directing the expression of a nucleic acid sequence encoding an enzyme of the invention; optionally a regulator of the promoter, a transcription start site, a translational start codon; and a nucleic acid sequence encoding an enzyme of the invention.

The vector may also contain one or more selectable marker genes, for example one or more antibiotic resistance genes. Such marker genes allow identification of transformants. Optionally, the vector may also comprise an enhancer for the promoter. The vector may also comprise a polyadenylation signal, typically 3' to the nucleic acid encoding the enzyme of the invention. The vector may also comprise a transcriptional terminator 3' to the sequence encoding the enzyme of the invention.

The vector may also comprise one or more introns or other non-coding sequences, for example 3' to the sequence encoding the polypeptide of interest.

In a typical vector, the nucleic acid sequence encoding the enzyme of the invention is operably linked to a promoter capable of expressing the sequence. "Operably linked" refers to a juxtaposition wherein the promoter and the nucleic acid sequence encoding the enzyme of the invention are in a relationship permitting the coding sequence to be expressed under the control of the promoter. Thus, there may be elements such as 5' non-coding sequence between the promoter and coding sequence. Such sequences can be included in the vector if they enhance or do not impair the correct control of the coding sequence by the promoter.

Any suitable promoter capable of directing expression of the nucleic acid encoding the therapeutic polypeptide or protein may be included in the vector. For example, the promoter may be a bacterial, eukaryotic or viral promoter. The promoter may be constitutive or inducible.

Thus, the invention provides host cells comprising one or more recombinant nucleic acids of the invention. These cells are typically transformed or transfected with the recombinant nucleic acid. The recombinant nucleic acid may be introduced into the host cell by any suitable means. For example, sequences encoding enzymes of the invention may be packaged into infectious viral particles in order to transfect cells. The nucleic acid sequences encoding enzymes of the invention may also be introduced by electroporation, lipofection, biolistic transformation or by simply contacting the nucleic acid sequences with cells in solution.

Such vectors may replicate either after integration into the host cell genome or remain extrachromosomal, as in the case of plasmids. Any suitable host cell may be used, including both prokaryotic and eukaryotic microbes, and plant cells.

Recombinant clones may be selected using generally available techniques, such as screening for the presence of a marker. One suitable screening methods include nucleic acid hybridisation, antibody assays and plate assays for the detection of protein activity.

If the enzyme of interest is secreted, it may be recovered from the growth medium by conventional techniques. Alternatively, it can be recovered from the host cells by disrupting them, and then using recovery techniques known in the art.

*Thermopallium natronophilum*, a specific novel microorganism of this invention, has been found to produce valuable novel enzymes, in particular, amylases, cellulases, lipases, proteases, pullulanases and xylanases. As an illustration, the properties of the amylases of the invention will be described.

Properties of the Amylases Produced by the Microorganism

The molecular weight of the soluble amylase fraction separated from the growth medium by gel-filtration chromatography is 90 kDa, by comparison with protein markers. This amylase fraction has an optimum temperature for amylase activity of 95° C. and an optimum pH of 8.8.

Two amylases can be separated by ion exchange chromatography and give the following molecular weights when examined by SDS-polyacrylamide electrophoresis:

Amylase A-I subunit molecular weight=87 kDa
Amylase A-II subunit molecular weight=83 kDa.

Amylase A-I has an optimum temperature of 95° C. and optimum pH of 10.2. The half-life of its activity is 11 minutes measured at 96° C.

Amylase A-II has an optimum temperature of 80° C. and an optimum pH of 9.6. No enzyme activity is lost during incubation at 80° C. for 120 minutes.

The amylases have the following further characteristics.

| | |
|---|---|
| Amylase A-I: | Hydrolytic activity on soluble starch producing primarily maltose and other dextrins. Hydrolytic activity on pullulanan. Activity is enhanced by NaCl (0.0067M) |
| Amylase A-II: | Hydrolytic activity on soluble starch producing dextrins (G1–G9). Activity reduced by EDTA and EGTA. Requires $Ca^{2+}$ for activity. |

Amylase A-I has the N-terminal amino acid sequence:
  Xaa-Xaa-Glu-Ile-Ile-Tyr-Val/Asp-Gly-Phe (where Xaa represents any amino acid);
and contains the (internal) partial amino acid sequence:
  Tyr-Ile-Gly-Asp-Gly-Ala-(Trp)-Glu-Ala-Val-Leu-Glu-Gly-(Asp)-(Asp)-Glu-(Gly/Glu)-Phe-Tyr-Arg (where brackets indicate uncertainty about the identity of the amino acid).

Amylase A-II all comprises the (internal) partial amino acid sequence:
  Ile-Gly-Leu-Pro-Ser-Val-Met-Thr-Glu-Pro-Trp-Asn-Pro-Ile-Gly-Gly-Ser-Asn-(Trp)-Ile-Phe-Asp-Met-Met-Leu-Ile-(Arg).

Amylases A-I and A-II are preferred amylases of the invention, but the invention is not limited to these amylases. Rather, the invention also provides variants of these amylases with slightly different amino acid sequences, and the nucleic acid sequences encoding these variants.

A variant amylase of the invention typically has a high degree of sequence homology to Amylase A-I or Amylase A-II, for example up to 70%, up to 80%, up to 90%, up to 95%, or up to 99% sequence homology.

A variant may have a sequence which differs from that of Amylase A-I or Amylase A-II by one or more deletions, substitutions or insertions, as long as the variant has the amylase activity of Amylase A-I or Amylase A-II, or substantially that activity. For example, variants typically have hydrolytic activity on some or all of the substrates on which Amylase A-I and/or A-II have hydrolytic activity.

Utility of the Invention

Enzymes obtained from the novel organisms may be used in the detergent industry in laundry detergents and automatic dishwashing detergents. Due to their thermostability and alkaline nature, these enzymes are extremely suitable to be used at high temperatures at high pH. In other words, they are extremely suitable to be used under conditions which are ideal for washing, especially for dishwashing. Examples of enzymes which may be used in both powder and liquid detergents for the degradation of stains and soil are amylases for the degradation of carbohydrates, proteases for the degradation of protein and lipases for the degradation of lipids. If the enzymes are used in compositions, such as for example in detergent compositions, they may be used in combination with many other detergent ingredients known in the art as, for example, builders, bleaching agents, bleach activators, softeners, perfumes, other enzymes etc.

The detergent industry is not the only industry interested in thermostable alkaline enzymes. Many useful applications for these enzymes are also found in the paper and pulp industry and the textile industry. For instance, thermostable alkaline amylases may be used for laundry detergents and automatic dishwashing detergents, but also for the manufacture of paper, especially desizing, and desizing of textiles, especially in combination with an alkaline scouring process.

It is this versatility of thermostable alkaline enzymes that explains the growing demand for these enzymes.

EXAMPLES

Example 1

Cultivation of the Microorganism

Medium

*Thermopallium natronophilum* was cultivated in a medium having the following composition (per liter):

| | |
|---|---|
| 100 ml Solution A | |
| 10 ml Solution B | |
| 10 ml Solution C | |
| 5 ml Vitamin solution | (Raven et al. (1992) Appl. Microbiol. Biotech. 38, 263–267. or DSM 141). |
| 1 ml Resazurin solution | (1 g/L) (Sigma) |

11

-continued

| | | |
|---|---|---|
| 2 g | Tryptone (Difco Bacto) | |
| 1 g | Yeast extract (Difco Bacto) | |
| 2.5 g | Starch, soluble (BDH/Merck) | |
| 2 g | Sodium chloride | |
| 5 g | Sodium bicarbonate | |
| 0.5 g | Sodium sulphide.xH$_2$O | |

The pH was adjusted to pH 8.5 with 1M HCl or 20% v/v H$_2$O$_4$.

The medium was prepared under strictly anaerobic conditions.

Large Scale Growth Conditions

Cultures were grown in 20 liter volumes in glass reservoir bottles without pH control, at 65° C., under continuous sparging with oxygen-free nitrogen (0.1 vvm) through a P160 glass distribution tube (maximum porosity 160 μm). The sterile medium was inoculated with 1% of a pre-grown culture. Cells were grown for 18–21 hours, achieving an optical density (A$_{600}$) of 0.7 to 0.8. The cells were harvested by serial centrifugation (5000 rpm, 20 min., 4° C.) in a Sorvall RC3-B centrifuge. A typical biomass yield was 3.2–3.9 g/L wet weight. The cell paste was stored at −20° C.

Example 2

Enzyme Extraction

The cell paste (from Example 1) was diluted to 0.2 g/ml in buffer (0.05 M Tris, 0.005 M EDTA), pH 8.5). The mixture was sonicated at 0° C. using a 3 mm probe in a Ultrasonics Ltd., model SP-958 apparatus by applying 3×10 seconds of 50 W. The broken cell suspension was centrifuged at 20,000 rpm for 20 min. at 5° C. (Sorvall, rotor SM-24). The cell pellet was re-suspended in buffer, mixed and re-centrifuged. The 2 supernatant fractions were combined.

Alternatively, a concentrated suspension of cells was defrosted and 6 N NaOH was added to raise the pH to 12. The mixture was incubated overnight at room temperature. The pH was re-adjusted with acid to pH 8–10, the mixture centrifuged at 20,000 rpm for 40 min, and the supernatant collected.

Example 3

Purification of Amylase Enzymes

The supernatant (from Example 2) was concentrated to 1.5 to 2 ml by ultra-filtration in a Centriprep-30 unit (Amicon) using a membrane having a 10 kDa molecular weight cut-off. The concentrated protein was subjected to gel-filtration on a HR 16/60 Superdex-200 column which was eluted with 0.02 M Tris buffer (pH 8.5) at a flow rate of 1 ml/min. Fractions containing amylase activity were combined and subjected to ion-exchange chromatography on a HR 5/5 Mono Q column. Protein was eluted with a salt gradient of 0–2 M NaCl in 0.02 M Tris buffer, pH 8.5 at a flow rate of 0.75 ml/min. Two fractions of separate amylase activity were obtained which were combined and dialysed against 0.02 M Tris buffer, pH 8.5. A further purification of the individual amylase proteins was accomplished by a further application of ion-exchange chromatography. Two fractions of amylase activity were obtained, amylase A-I and amylase A-II. The two amylase components were examined by SDS-PAGE which indicated subunit molecular weights of 87 kDa and 83 kDa for A-I and A-II, respectively.

12

Example 4

Assays for Amylase Activity

Method 1 A modified Bernfeld assay was used (Bernfeld, P. (1955) in: *Methods in Enzymology*, vol. 1 (S. P. Colowick and N. O. Kaplan, Eds.) Academic Press, New York, pp 149–158). 100 μl of enzyme sample was incubated at 80° C. with 425 μl of buffer (0.05 M Tris, 0.005 M EDTA, 0.0067 M NaCl [pH 8.5 at 20° C., pH 8 at 80° C.]), 150 μl of substrate (0.05 M Tris, 0.005 M EDTA, 0.0067 M NaCl, 1% (w/v) soluble potato starch (Sigma), pH 8.5 at 20° C.) and 75 μl of 0.002 M CaCl$_2$ for 20 minutes. The reaction was terminated with developing solution (1% w/v 3,5-dinitrosalicylic acid in 0.4 M NaOH) and boiled for 5 minutes. The assay mixture was cooled on ice and the absorbance measured at 550 nm and read against a calibration curve constructed using maltose instead of enzyme.

Method 2 A 100 μl enzyme sample was incubated at 70° C. with 900 μl substrate solution (1% w/v soluble starch in 0.005 M MES/HEPES/glycine buffer, pH 8.0) for 60 minutes. The reaction was terminated by the addition of 10 μl 6 N HCl and developed by the addition of 1 ml of iodine solution (Sigma, P700-2; diluted 1:3) to 100 μl of reaction mixture. The absorbance was measured at 620 nm against water and compared to a standard calibration curve constructed using a standard α-amylase (Maxamyl S3) with an α-amylase activity of 82650 TAU/g.

Method 3 (for amylase A-I) Conditions were identical to Method 1 except that the enzyme sample was incubated with 650 μl of substrate (0.05 M Tris, 1% w/v soluble potato starch, 0.0067 M NaCl, pH 8.5 at 20° C.).

Method 4 (for amylase A-II) Conditions were identical to Method 1 except that the enzyme sample was incubated with 650 μl substrate solution (0.05 M Tris, 1% w/v soluble potato starch, 0.002 M CaCl$_2$, pH 8.5 at 20° C.).

Example 5

Effect of Temperature on Enzyme Activity

In a first test, the unpurified enzyme derived from the grown cells according to Example 2, and separated by gel-filtration chromatography (Example 3) was assayed for amylase activity in the range 60° to 105° C. Enzyme activity was measured in 0.05 M Tris buffer according to assay Method 1 of Example 4. The results show an optimum temperature for activity of 95° C., as presented in FIG. 2.

In a second test, the purified amylase A-I obtained according to Example 3 was assayed in the range 65° to 100° C. Enzyme activity was measured according to assay Method 3 of Example 4.

The results show an optimum temperature for activity of 95° C., with 50% of the maximum activity displayed in the range 88° to 99° C.

In a third test, the purified amylase A-II obtained according to Example 3 was assayed in the range 65° to 100° C. Enzyme activity was measured according to assay Method 4 of Example 4.

The results show a broad profile with an optimum temperature for activity of 80° C., with 50% of the maximum activity in the range <65° to 96° C.

Example 6

Effect of pH on Enzyme Activity

In a first test, the unpurified enzyme derived from the grown cells according to Example 2, and separated by gel-filtration chromatography (Example 3) was assayed for amylase activity in a pH range from pH 6.0 to 10.8. Enzyme activity was measured at 80° C. according to assay Method 1 of Example 4, and by substituting Tris buffer with an appropriate buffer (MES, HEPES or glycine) for the pH range required.

The results show a broad optimum between pH 7.5 and pH 9.5 with a maximum activity of pH 8.8.

In a second test, the purified amylase A-I obtained according to Example 3 was assayed in the pH range 4.1 to 11.4 by employing appropriate buffers (acetate, MOPS, MES, Tris, HEPES, diethanolamine or glycine). Enzyme activity was measured at 80° C. according to assay Method 3 of Example 4.

The results show an optimum pH for activity of amylase A-I of pH 10.2.

In a third test, the purified amylase A-II obtained according to Example 3 was assayed in the pH range 4.1 to 11.4 by employing appropriate buffers (acetate, MOPS, MES, Tris, HEPES, diethanolamine or glycine). Enzyme activity was measured at 80° C. according to assay Method 3 of Example 4.

The results show an optimum pH for activity of amylase A-II of pH 9.6, with 50% of the maximum activity in the range pH8.1 to >pH 11.5.

Example 7

Amino Acid Sequence Analysis of the Amylases

The N-terminal amino acid sequence of the amylase A-I having a molecular weight of 87 kDa, obtained according to Example 3 was determined by EUROSEQUENCE (Groningen, The Netherlands).

The N-terminal amino acid sequence (SEQ ID No. 2 of the attached sequence listing) was assigned as:

Xaa-Xaa-Glu-lle-lle-Tyr-Val/Asp-Gly-Phe (where Xaa indicates any amino acid).

A further fragment of the amylase A-I protein yielded an amino acid sequence (SEQ ID No. 3 of the attached sequence listing) as follows:

Tyr-lle-Gly-Asp-Gly-Ala-(Trp)-Glu-Ala-Val-Leu-Glu-Gly-(Asp)-(Asp)-Glu-(Glu/Gly)-Phe-Tyr-Arg (where brackets indicate uncertainty about the identity of the amino acid).

Similarly, amylase A-II, a protein of 83 kDa, obtained according to Example 3 provided a partial amino acid sequence (SEQ ID No. 4 of the attached sequence listing) as follows:

lle-Gly-Leu-Pro-Ser-Val-Met-Thr-Glu-Pro-Trp-Asn-Pro-lle-Gly-Gly-Ser-Asn-(Trp)-lle-Phe-Asp-Met-Met-Leu-lle-(Arg).

Example 8

Isolation of Amylase Genes

A genomic library of the strain Tg9a was constructed in plasmid pTZ18R (Mead, D. A. et al. (1986) Protein Engineering 1, 67). Chromosomal DNA of *Thermopallium natronophilum* Tg9A was digested with HindIII and EcoR1. Restriction fragments were size fractionated by agarose gel electrophoresis and fragments of 1 kb and greater were isolated from the gel. This fraction was ligated to HindIII/EcoR1 digested DNA from the vector pTZ18R. The ligate was transformed to *E. coli* XL1 Blue MRF by electroporation. Recombinant clones were screened on amylose azure agar. Clones that exhibited clearing zones around the colony were isolated. The amylase activity of the recombinant strains was determined after growth for 24 hours at 37° C. in LB-medium (Miller, J. H. (1972) Experiments in Molecular Genetics, Cold Spring Harbor Laboratory, page 433).

The plasmid DNA of the recombinant strains can be isolated and the inserts characterised by restriction analysis.

What is claimed is:

1. An isolated alkaline amylase native to *Thermopallium natronophilum* having a molecular weight of 83kDa as measured on SDS-PAGE and comprising a peptide region having an internal amino acid sequence as shown in SEQ ID NO: 4 obtained by culturing Thermopallium capable of producing the amylase under conditions conducive to the production of the amylase and recovering said amylase wherein the amylase exhibits hydrolytic activity on soluble starch producing dextrins.

2. An isolated alkaline pullulanase native to *Thermopallium natronophilum* having a molecular weight of 87 kDa as measured on SDS-PAGE and comprising a peptide region having an N-terminal amino acid sequence shown in SEQ ID No.2, and a peptide region having an internal amino acid sequence as shown in SEQ ID No.3.

3. The isolated alkaline pullulanase of claim 2 wherein 50% of the maximum activity is displayed in the temperature range of 88 to 99° C.

4. The isolated alkaline amylase of claim 2 wherein said pullulanase is derived from *Thermopallium natronophilum* Tg9A, Accession Number DSM 9460.

5. A composition comprising the alkaline amylase as defined in claim 1.

6. The composition according to claim 5, wherein the composition is a detergent composition.

7. A composition comprising a pullulanase as defined in claim 2.

8. A composition according to claim 7, wherein the composition is a detergent composition.

9. A method for the formulation of a detergent composition comprising adding the isolated alkaline amylase according to claim 1 in combination with other detergent ingredients selected from the group consisting of builders, bleaching agents, bleach activators, softeners, perfumes and other enzymes and forming a detergent composition.

10. A method for the formulation of a detergent composition comprising, adding the isolated alkaline pullulanase according to claim 2 in combination with other detergent ingredients selected from the group consisting of builders, bleaching agents, bleach activators, softeners, perfumes and other enzymes; and forming a detergent composition.

* * * * *